(12) United States Patent
Han et al.

(10) Patent No.: US 10,180,418 B2
(45) Date of Patent: Jan. 15, 2019

(54) LENS-ATTACHED TISSUE CELL PRESSURIZATION DEVICE

(71) Applicant: Korea Institute of Industrial Technology, Chungcheongnam-do (KR)

(72) Inventors: Sang Kuy Han, Chungcheongnam-do (KR); Walter Herzog, Calgary (CA); Hyun Jong Shin, Daejeon (KR)

(73) Assignee: KOREA INSTITUTE OF INDUSTRIAL TECHNOLOGY, Gyeonggi-Do (KR)

( * ) Notice: Subject to any disclaimer, the term of this patent is extended or adjusted under 35 U.S.C. 154(b) by 0 days.

(21) Appl. No.: 15/511,704

(22) PCT Filed: Oct. 30, 2014

(86) PCT No.: PCT/KR2014/010292
§ 371 (c)(1),
(2) Date: Mar. 16, 2017

(87) PCT Pub. No.: WO2016/043375
PCT Pub. Date: Mar. 24, 2014

(65) Prior Publication Data
US 2017/0261488 A1  Sep. 14, 2017

(30) Foreign Application Priority Data

Sep. 17, 2014 (KR) .......................... 10-2014-0123796

(51) Int. Cl.
*G02B 21/00* (2006.01)
*G01N 33/483* (2006.01)
(Continued)

(52) U.S. Cl.
CPC ......... *G01N 33/4833* (2013.01); *G02B 21/00* (2013.01); *G02B 21/0004* (2013.01); *G02B 21/02* (2013.01); *G01L 5/0038* (2013.01)

(58) Field of Classification Search
CPC .. G01N 33/48; G01N 33/483; G01N 33/4833; G02B 21/00; G02B 21/02; G01L 5/00; G01L 5/0028; G01L 5/0038
(Continued)

(56) References Cited

U.S. PATENT DOCUMENTS 2,216,943 A * 10/1940 Hanemann ............. G02B 21/02
125/39
6,033,913 A * 3/2000 Morozov .................. G01N 3/04
436/86

(Continued)

FOREIGN PATENT DOCUMENTS

JP  H06076332 A   3/1994
JP  2005189859 A  7/2005
(Continued)

OTHER PUBLICATIONS

Int'l Search Report dated May 27, 2015 in Int'l Application No. PCT/KR2014/010292.

*Primary Examiner* — William R Alexander
(74) *Attorney, Agent, or Firm* — Cantor Colburn LLP

(57) ABSTRACT

Disclosed is a lens-attached tissue cell pressurization device that is selectively coupled to an objective lens to perform pressurization in an optical device configured measure a cell tissue using the objective lens, the lens-attached tissue cell pressurization device including: a body extending in a lengthwise direction of the objective lens such that at least a portion of the objective lens is inserted into the body and having a connector selectively fixed to the objective lens; and an indenter provided at a lower end of the body, having a penetration part formed at a center of the indenter, and pressurizing the cell tissue by a change in a relative location of the objective lens and the cell tissue.

6 Claims, 7 Drawing Sheets

(51) Int. Cl.
*G02B 21/02* (2006.01)
*G01L 5/00* (2006.01)

(58) Field of Classification Search
USPC .......................................................... 359/656
See application file for complete search history.

(56) References Cited

U.S. PATENT DOCUMENTS

| | | | |
|---|---|---|---|
| 9,810,683 B2* | 11/2017 | Gimzewski | G01J 3/453 |
| 2002/0018215 A1* | 2/2002 | Nakamura | G01B 11/255 |
| | | | 356/512 |
| 2007/0193346 A1* | 8/2007 | Bonin | G01N 3/48 |
| | | | 73/81 |
| 2010/0107745 A1* | 5/2010 | Bonin | G01N 3/42 |
| | | | 73/105 |
| 2010/0284016 A1* | 11/2010 | Teitell | G01J 3/453 |
| | | | 356/451 |
| 2014/0080171 A1* | 3/2014 | Gimzewski | G01J 3/453 |
| | | | 435/29 |
| 2017/0248518 A1* | 8/2017 | Nadkarni | G01N 21/4788 |

FOREIGN PATENT DOCUMENTS

| | | | |
|---|---|---|---|
| JP | 2008225218 A | 9/2008 |
| KR | 1020100018515 A | 2/2010 |
| KR | 1020100080532 A | 7/2010 |

* cited by examiner

LENS-ATTACHED TISSUE CELL PRESSURIZATION DEVICE

CROSS-REFERENCE TO RELATED APPLICATION

This application is a Section 371 of International Application No. PCT/KR2014/010292, filed Oct. 30, 2014, which was published in the Korean language on Mar. 24, 2016 under International Publication No. WO 2016/043375 A1, and the disclosure of which is incorporated herein by reference.

TECHNICAL FIELD

The present invention relates to a lens-attached tissue cell pressurization device that is separately attached to a lens for optically measuring an object, to pressurize the object and stably observe a change of the object depending on the pressurization.

BACKGROUND ART

In recent years, with the aging of the population, various researches for developing fundamental treatment methods for patients as well as simply curing diseases of humans have been progressed by identifying characteristics of body tissues and researching the same.

In particular, a separate optical device has been used to not only simply analyze shapes of tissues having constant elasticity such as a knee cartilage among cell tissues of a body of a human and but also measure changes of the tissues in accordance with changes in external factors such as pressure and temperature.

The cell tissues of the knee cartilage are cell tissues that support a weight of a person, the shapes of the cell tissues are changed in accordance with pressure, and researches for analyzing changes in the shapes of the cell tissues by separately pressurizing the cell tissues and observing the changes of the cell tissues have been progressed to observe the changes in the shapes of the cell tissues.

In the conventionally-used cell tissue observation method for progressing the above-described researches, when cell tissues are observed by the optical device, a focal distance is set after a spaced distance between the optical device and the cell tissue is fixed. Further, mainly changes of the cell tissues are observed through the optical device by pressurizing the cell tissues through a separate pressurization means.

However, the above method has a problem in that the separate pressurization means is further provided and has a problem in that it is difficult that the method is applied to the conventionally-used optical device such as an optical microscope.

In addition, when an artificial tissue using a stem cell which is recently and frequently introduced as a new research field is developed, a newly-developed measurement device that simultaneously performs biological measurement and mechanical and physical measurement for mechanical and biological verification of tissues and cells has been required.

DISCLOSURE

Technical Problem

The present invention is conceived to solve the above-described problems, and a technical aspect of the present invention is to provide a lens-attached tissue cell pressurization device that is selectively coupled to an objective lens for observing an object to be measured to pressurize cell tissues, and at the same time, may maintain a spaced distance between the objective lens and a measurement lens to maintain focusing of the objective lens.

A technical aspect to be achieved by the present invention is not limited to the above-described technical aspect, and not-mentioned other technical aspects should be clearly understood by those skilled in the art to which the present invention pertains, based on the following description.

Technical Solution

The present invention is conceived to solve the above technical problems, and a lens-attached tissue cell pressurization device that is selectively coupled to an objective lens to perform pressurization in an optical device configured measure a cell tissue using the objective lens, according to an aspect of the present invention, includes: a body extending in a lengthwise direction of the objective lens such that at least a portion of the objective lens is inserted into the body and having a connector selectively fixed to the objective lens; and an indenter provided at a lower end of the body, having a penetration part formed at a center of the indenter, and configured to pressurize the cell tissue by a change in a relative location of the objective lens and the cell tissue.

Further, the indenter is spaced apart from a lower end of the objective lens by a predetermined distance, and a spaced distance between the indenter and the objective lens is maintained.

Further, the body is configured such that the spaced distance between the indenter and the objective lens is selectively adjusted.

Further, the body includes a fixing member having the connector and selectively fixed to the objective lens, and a movable member which is rotated together with the fixing member and of which a length is selectively adjusted depending on rotation to adjust the spaced distance between the indenter and a lower end of the objective lens.

Further, the lens-attached tissue cell pressurization device further includes a pressure measuring means arranged on the indenter to measure a degree of pressure applied to the cell tissue by the indenter.

Further, the pressure measuring means has an upper cell having first coupling parts protruding in a transverse direction from a lower portion of the body and coupled to the body and a lower cell having second coupling parts protruding in a transverse direction from a lower portion of the upper cell and coupled to the indenter.

Further, the first coupling parts and the second coupling parts are arranged to cross each other, and are coupled to the upper cell and the lower cell, respectively.

Further, the penetration part is formed of an optically transparent material, is in contact with the cell tissue and is formed to correspond to a location of the objective lens such that the cell tissue is projected onto the penetration part and is observed through the objective lens.

Advantageous Effects

A lens-attached tissue cell pressurization device according to the present invention has the following effects.

First, the lens-attached tissue cell pressurization device has an advantage in that a tissue cell pressurization device having a body surrounding a portion of an objective lens of an optical device and an indenter provided below the body to maintain a predetermined spaced distance between the indenter and the objective lens is coupled, and thus even when cell tissues are pressurized by the indenter, the spaced distance between the objective lens and the indenter is maintained, so that the cell tissues may be observed even without additional adjustment of a focus of the objective lens.

Second, the lens-attached tissue cell pressurization device has an advantage in that a separate pressure measuring means is provided between the indenter and the body, so that a degree of pressure applied to cells by the indenter may be measured.

Such effects by the present invention are not limited to the above-described effects, and other not-mentioned effects could be clearly understood by those skilled in the art with reference to the appended claims.

BEST MODE FOR THE INVENTION

Hereinafter, embodiments of the present invention will be described in detail with reference to the accompanying drawings. However, in description of the present invention, descriptions of the widely-known functions or configurations will be omitted to make the subject matter of the present invention clear.

In addition, in description of the present invention, the terms indicating directions, such as a front side, a rear side, an upper side and a lower side, are written such that those skilled in the art may clearly understand the present invention, and indicate relative directions. Accordingly, the scope of a right is not limited by the terms.

A lens-attached tissue cell pressurization device according to the present invention is a device that may be coupled to an objective lens to pressurize the cell tissues and, at the same time, photograph tissues and cells deformed by the pressurization in an optical device for observing cell tissues using an objective lens.

In general, an optical device is widely used to pressurize cell tissues such as knee cartilages, spinal disks and artificial tissues generated by stem cells when the cell tissues are observed and observe changes of the cell tissues depending on a change in pressure. Here, it is general that a separate pressurization means for pressurizing the cell tissues is provided to pressurize the cell tissues and observe the same using the optical device.

However, unlike this, the lens-attached tissue cell pressurization device according to the present invention may be coupled to the objective lens to pressurize the cell tissues and, at the same time, allow a user to consistently observe the pressurized cell tissues through the objective lens.

First, configurations of the lens-attached tissue cell pressurization device will be schematically described below with reference to FIGS. 1 to 3.

Figure 1:
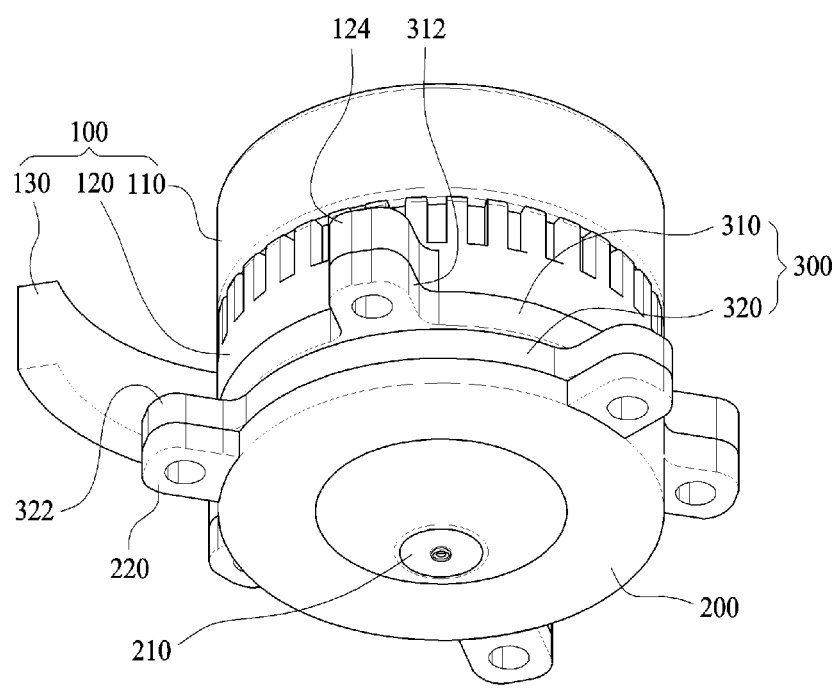
FIG. 1 is a view schematically illustrating a lens-attached tissue cell pressurization device according to the present invention.
Figure 2:
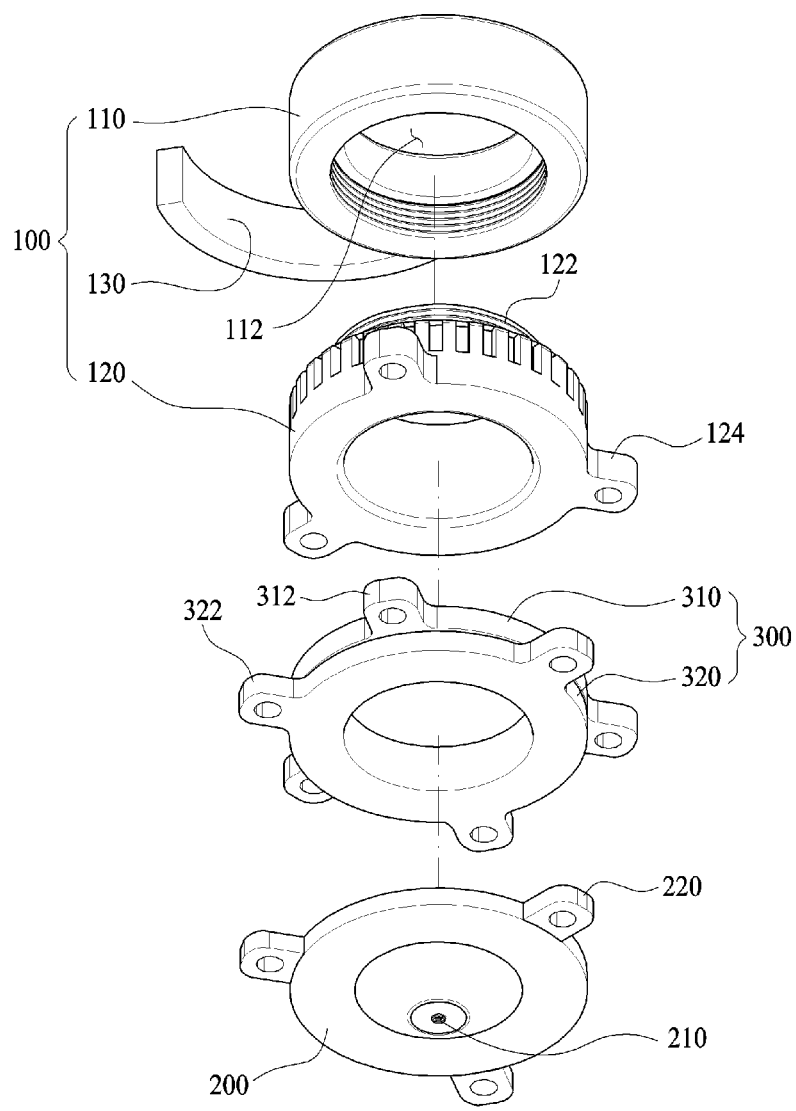
FIG. 2 is an exploded perspective view illustrating the lens-attached tissue cell pressurization device of FIG. 1.
Figure 3:
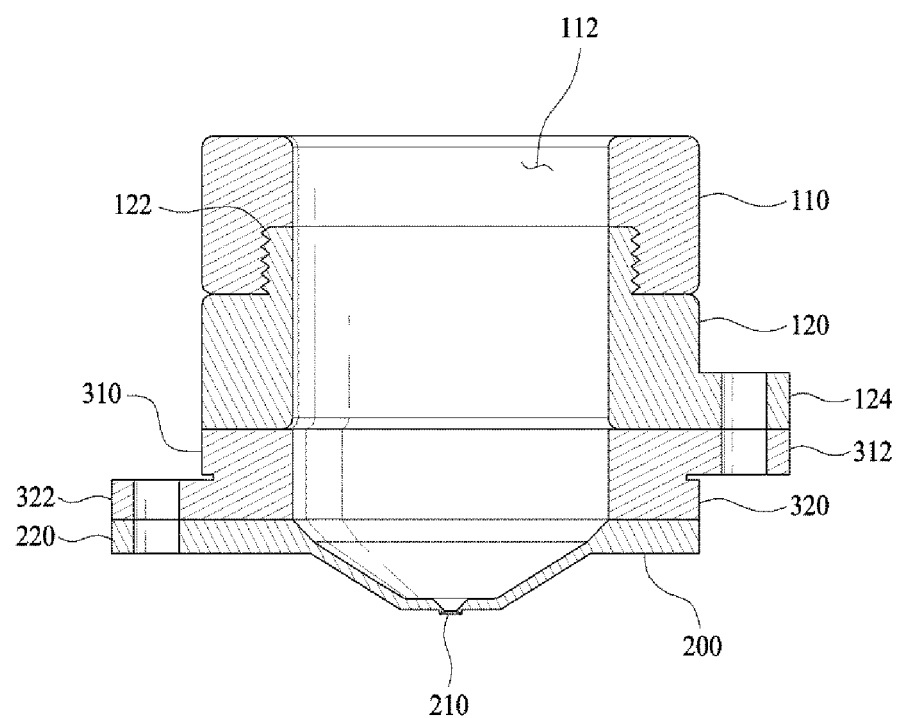
FIG. 3 is a sectional view illustrating the lens-attached tissue cell pressurization device of FIG. 1.

FIG. 1 is a view schematically illustrating a configuration of the lens-attached tissue cell pressurization device according to the present invention, FIG. 2 is an exploded perspective view illustrating the configuration of the lens-attached tissue cell pressurization device of FIG. 1, and FIG. 3 is a sectional view illustrating an inner configuration of the lens-attached tissue cell pressurization device of FIG. 1.

The lens-attached tissue cell pressurization device according to the present invention includes a body 100, an indenter 200 and a pressure measuring means 300.

The body 100 extends along a lengthwise direction of the objective lens 10, and at least a portion of the objective lens 10 is inserted into the body 100. Further, in a state in which the objective lens 10 is selectively inserted into the body 100, the body 100 is fixed to the objective lens 10.

That is, the body 100 has a space formed therein along the lengthwise direction and the objective lens 10 is inserted into the body 100 so that the body 100 is coupled to the objective lens 10 while the objective lens surrounds the space.

In detail, the body 100 according to the present embodiment may mainly include a connector 130, a fixing member 110 and a movable member 120, as illustrated.

The fixing member 110 is communicated forward/rearward along a lengthwise direction thereof such that the objective lens 10 passes therethrough and the connector 130 is provided on one side of the fixing member 110 so that the fixing member 110 is selectively coupled to the objective lens 10.

Here, the fixing member 110 has a hole 112 formed therein through which a portion of the objective lens 10 passes and allows a portion of the objective lens 10 together with the movable member 120, which will be described below, to be located therein.

Meanwhile, the connector 130 is a means for fixing the fixing member 110 and the objective lens 10 to each other. In the present embodiment, as illustrated, in a state in which the objective lens 10 is inserted into the fixing member 110, the objective lens 10 is pressurized and fixed.

In detail, as illustrated, the connector 130 may protrude from one side of the fixing member 110, may be selectively tilted, and may be pressurized while surrounding a side surface of the objective lens 10 inserted into the fixing member 110, depending on a tilting state, to adjust a fixing state of the fixing member 110 and the objective lens 10.

Of course, unlike this, the connector 130 may be formed to have various shapes, and may have any shape that may adjust the fixing state of the objective lens 10 and the fixing member 110.

Meanwhile, the movable member 120 is provided below the fixing member 110 and has an inner space which is formed through a hole continuing from the hole 112 formed in the fixing member 110 and in which the objective lens 10 is located.

That is, the movable member 120 is provided below the fixing member 110 to surround the objective lens 10 on a lower side thereof together with the fixing member 110.

Here, the movable member 120 extends to continue from the fixing member 110 and is configured such that a location thereof is adjusted along a lengthwise direction thereof.

In detail, the movable member 120 is configured such that a coupling length of the movable member 120 and the fixing member 110 is selectively adjusted when the movable member 120 is coupled to the fixing member 110. In the present embodiment, as illustrated in FIG. 3, a thread 122 is formed on the movable member 120 along a circumference of the movable member 120 and a lower portion of the fixing member 110 is formed to correspond to the thread 122 so that the fixing member 110 and the movable member 120 are coupled to each other through rotation.

Further, the location of the movable member 120 is adjusted through relative rotation of the movable member 120 and the fixing member 110, so that a spaced distance between the indenter 200, which will be described below, and the objective lens 10 is adjusted.

That is, the entire length of the body 100 is adjusted depending on a rotation state of the movable member 120, and a detailed operation state thereof will be described in detail with reference to FIG. 6.

In this way, the body 100 according to the present invention includes the connector 130, the movable member 120 and the fixing member 110, and is selectively fixed to the objective lens 10 in a state in which a portion of the objective lens 10 is inserted into the inner space along the lengthwise direction thereof.

Meanwhile, the indenter 200 according to the present invention is provided at a lower end of the body 100 and has a penetration part 210 formed at a center thereof. Further, a cell tissue C is pressurized due to a change in a relative location of the objective lens 10 and the cell tissue C.

In detail, the indenter 200 is provided at a lower end of the body 100 along a lengthwise direction of the body 100 and a center of the indenter 200 protrudes downward. Here, the cell tissue C is located below the indenter 200.

Further, the penetration part 210 which is formed of a transparent material and through which the cell tissue C is projected onto the object lens 10 is provided at the center of the indenter 200. Here, as illustrated, the penetration part 210 is formed of a transparent material, is in contact with the cell tissue C and is formed to correspond to a location of the objective lens 10 such that the cell tissue C is projected thereonto and may thus be observed through the objective lens 10.

That is, the penetration part 210 is formed at a location vertically corresponding to a lens part provided at a lower end of the objective lens 10 to prevent an interference in observation of the cell tissue C through the objective lens 10 from being generated.

Meanwhile, the indenter 200 is formed at a lower end of the body 100 and, at the same time, is spaced apart from the objective lens 10 by a predetermined distance.

In this way, when the indenter 200 is spaced apart from the objective lens 10 by a predetermined distance, the user fixes a focus of the objective lens 10 to a location of the penetration part 210, and then observes the cell tissue C in a state in which the indenter 200 is in contact with the cell tissue C.

Here, the indenter 200 is fixedly coupled to a lower end of the body 100, so that the spaced distance between the indenter 200 and the objective lens 10 is not changed even when the cell tissue C is pressurized by the indenter 200.

As the indenter 200 is configured in this way, the user may consistently observe the cell tissue C while the optical device is focused, even when the cell tissue C is pressurized by the indenter 200 by adjusting a location of a stage S (see FIG. 4) on which the objective lens 10 or the cell tissue C is seated.

Meanwhile, the pressure measuring means 300, which is a means arranged on the indenter 200 to measure a degree of pressure applied to the cell tissue C by the indenter 200, may identify a strength of pressure applied to the cell tissue C, by measuring pressure applied to the indenter 200.

In the present embodiment, a general load cell may be employed as the pressure measuring means 300, and the pressure measuring means 300 is provided between the indenter 200 and the body 100 to measure a degree of pressure generated when the cell tissue C is pressurized by the indenter 200.

In detail, in the present embodiment, as illustrated, the pressure measuring means 300 is partitioned into an upper cell 310 and a lower cell 320 between the indenter 200 and the body 100 in a lengthwise direction thereof, and the cells are coupled to the body 100 and the indenter 200, respectively.

The upper cell 310 has first coupling parts 312 protruding in a transverse direction thereof from a lower portion of the body 100 and is coupled to the body 100. Further, the lower cell 320 has second coupling parts 322 protruding in a transverse direction from below in a state in which the upper cell 310 is stacked on the lower cell 320 and is coupled to the indenter 200.

As illustrated, the body 100 and the indenter 200 have first coupling bosses 124 correspondingly coupled to the first coupling parts 312 and second coupling bosses 220 correspondingly coupled to the second coupling parts 322, respectively.

In this way, the body 100 has the first coupling bosses 124 to be coupled to the first coupling parts 312 and is thus coupled to the upper cell 310. Further, the indenter 200 has the second coupling bosses 200 to be coupled to the second coupling parts 322 and is thus coupled to the lower cell 320.

Accordingly, the pressure measuring means 300 is arranged between the body 100 and the indenter 200 in a stacked state.

Further, the pressure measuring means 300 measures a degree of pressure generated as the cell tissue C is pressurized by the indenter 200, and displays the degree of pressure to the user through a display (not illustrated).

Here, the first coupling parts 312 and the second coupling parts 322 are arranged to cross each other along a vertical direction. That is, as illustrated, the first coupling parts 312 and the second coupling parts 322 are not located in the same line in a vertical direction (a lengthwise direction of the body 100) but are arranged to cross each other, so that an interference when the first coupling parts 312 and the second coupling parts 322 are coupled to the first coupling bosses 124 and the second coupling bosses 200, respectively, is prevented from being generated.

When the first coupling parts 312 and the second coupling parts 322 are located in the same line, an interference is generated between the upper cell 310 and the lower cell 320, so that applied pressure may not be accurately measured. Accordingly, the pressure applied to the cell tissue C by the indenter 200 may not be accurately measured.

As the pressure measuring means 300 is configured in this way, pressure applied between the indenter 200 and the body 100 is measured, and accordingly, the pressure applied to the cell tissue C by the indenter 200 may be measured.

In detail, the degree of pressure applied to the cell tissue C may be derived based on the pressure measured through the pressure measuring means 300 and a contact area of the indenter 200 and the cell tissue C.

As above, the lens-attached tissue cell pressurization device according to the present invention includes the body 100, the indenter 200 and the pressure measuring means 300. Further, the cell tissue C is pressurized by the intender 200 by adjusting a relative location of the cell tissue C and the objective lens 10, and at the same time, focusing of the objective lens 10 is maintained, so that the cell tissue C may be consistently observed.

At the same time, a change of the cell tissue C may be observed based on the change in pressure applied to the cell tissue C, by measuring the degree of pressure applied to the cell tissue C by the indenter 200.

Herein, a process of observing a change of the cell tissue C while pressurizing the cell tissue C through the lens-attached tissue cell pressurization device according to the present invention will be described below with reference to FIGS. 4 and 5.

Figure 4:
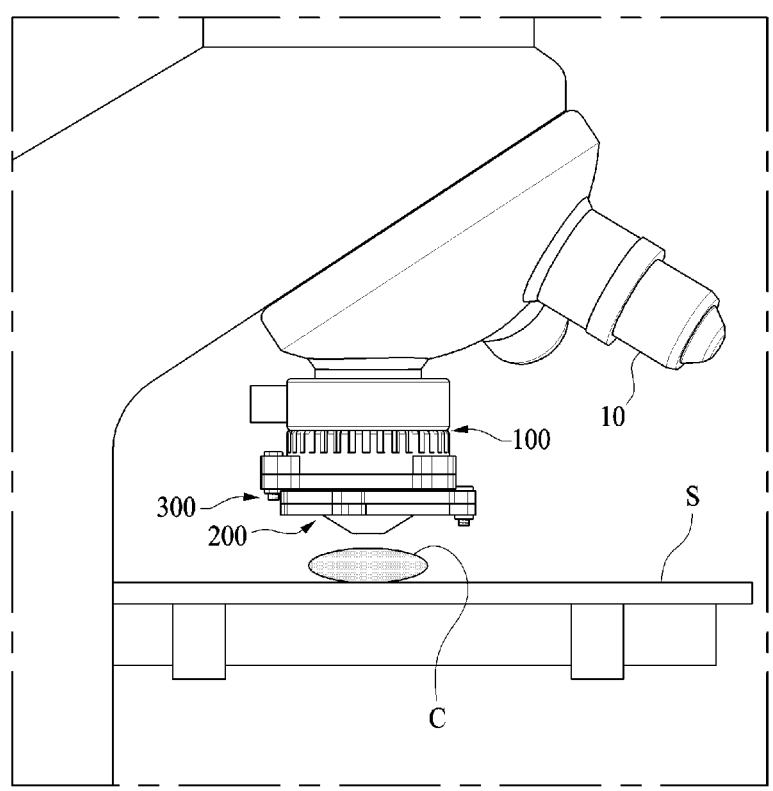
FIG. 4 is a view illustrating a state in which the lens-attached tissue cell pressurization device of FIG. 1 is coupled to an objective lens.
Figure 5:
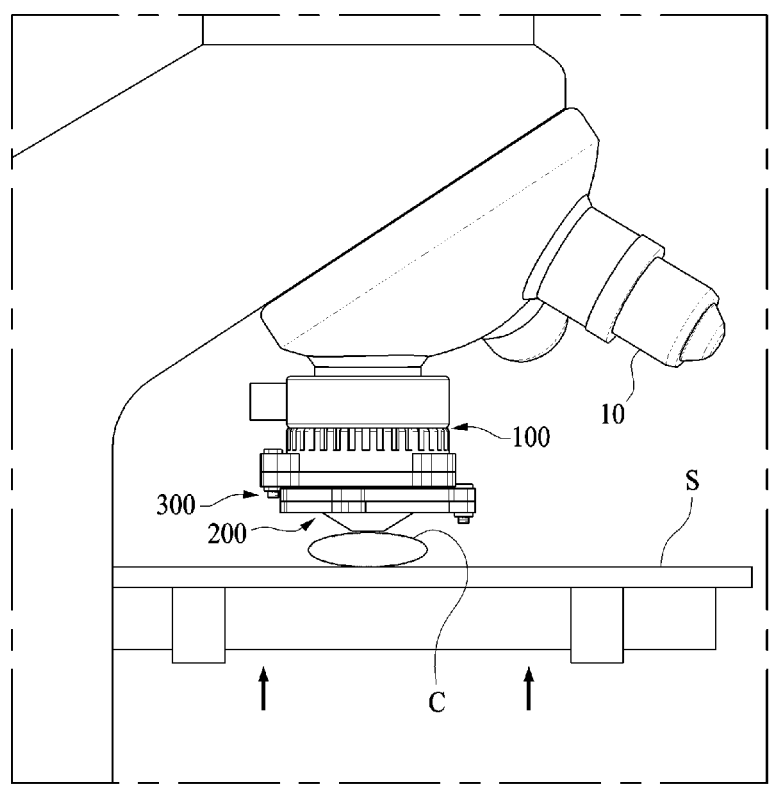
FIG. 5 is a view illustrating a state in which the lens-attached tissue cell pressurization device of FIG. 4 pressurizes cell tissues as the objective lens is moved.

FIG. 4 is a view illustrating a state in which the lens-attached tissue cell pressurization device of FIG. 1 is coupled to the objective lens 10, and FIG. 5 is a view illustrating a state in which the lens-attached tissue cell pressurization device of FIG. 4 pressurizes the cell tissue C as the objective lens 10 is moved.

First, FIG. 4 illustrates a state in which the lens-attached tissue cell pressurization device according to an embodiment of the present invention is coupled to the objective lens 10, wherein the indenter 200 is arranged above the cell tissue C.

Here, as illustrated, the cell tissue C is seated on the stage S, and external pressure is not applied thereto.

Further, the indenter 200 is spaced apart from the lower end of the objective lens 10 by a predetermined distance such that the spaced distance is maintained.

In this arrangement, as illustrated in FIG. 5, when a relative spaced distance between the cell tissue C and the objective lens 10 becomes smaller, the cell tissue C is pressurized by a protruding portion of the indenter 200.

Here, the spaced distance between the objective lens 10 and the cell tissue C is adjusted as the objective lens 10 is lowered and the stage S is elevated.

In this way, as the cell tissue C is pressurized by the indenter 200, the cell tissue C is changed, and the user observes or photographs the same.

Here, because a spaced distance between the indenter 200 and the lower end of the objective lens 10 is fixed, the focus of the objective lens 10 is not changed, and accordingly, the user may stably observe the cell tissue C even in a state in which the cell tissue C is pressurized by the indenter 200.

That is, even when the cell tissue C is pressurized after the user adjusts the focus of the objective lens to a location of the indenter 200, the cell tissue C may be observed with no need to additionally adjust the focus of the objective lens 10.

Meanwhile, the focus of the objective lens 10 is located at the penetration part 210 even when the cell tissue C is pressurized by the indenter 200, so that the cell tissue C is projected onto the penetration part 210 and is thus observed through the objective lens 10.

Further, the pressure applied to the cell tissue C by the indenter 200 may be consistently measured through the pressure measuring means 300 located between the indenter 200 and the body 100.

Accordingly, the user may observe the change of the cell tissue C based on the change in the pressure applied to the cell tissue C, through the pressure measuring means 300.

Next, a state in which the spaced distance between the indenter 200 and the objective lens 10 is adjusted in the tissue cell pressurization device according to the present invention will be described below with reference to FIGS. 6 and 7.

Figure 6:
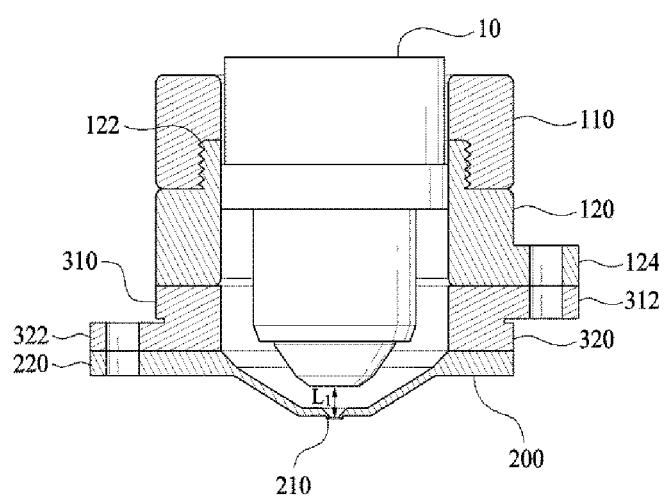
FIG. 6 is a view illustrating a state in which a spaced distance between the indenter and the objective lens is adjusted in the lens-attached tissue cell pressurization device of FIG. 1.
Figure 7:
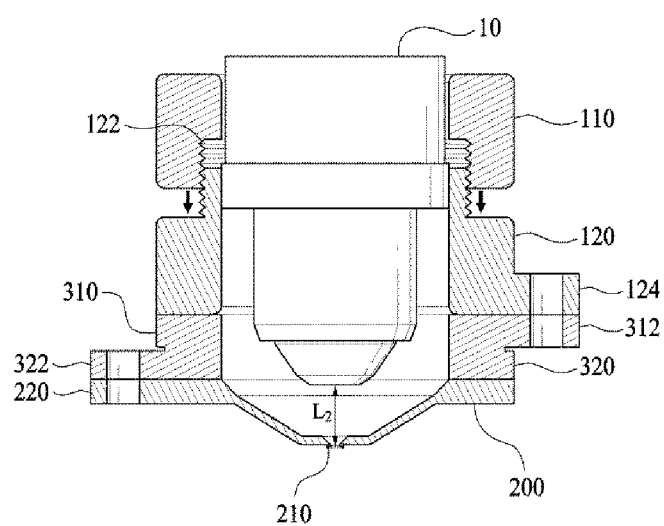
FIG. 7 is a view illustrating a state in which a spaced distance between the indenter and the objective lens is increased in the lens-attached tissue cell pressurization device of FIG. 6.

FIG. 6 is a view illustrating a state in which the spaced distance between the indenter 200 and the objective lens 10 is adjusted in the lens-attached tissue cell pressurization device of FIG. 1, and FIG. 7 is a view illustrating a state in which the spaced distance between the indenter and the objective lens is increased in the lens-attached tissue cell pressurization device of FIG. 6.

Referring to the illustrated drawings, as described above, the lens-attached tissue cell pressurization device according to the present invention includes the body 100, the indenter 200 and the pressure measuring means 300. Here, the body 100 includes the fixing member 110 and the movable member 120, and the entire length of the body 100 is adjusted by adjusting a location of the movable member 120.

In detail, the above-described movable member 120 has the thread 122 on an outer side surface thereof, the fixing member 110 is formed to correspond to the thread 122, and a portion of the fixing member 110 is inserted and fixed.

Accordingly, as illustrated in FIG. 6, as the fixing member 110 is inserted into the movable member 120, mutual coupling therebetween is maintained and a state in which the indenter 200 and the objective lens 10 is spaced apart from each other is maintained.

Here, as illustrated in FIG. 6, the spaced distance between the lower end of the objective lens 10 and the indenter 200 is L1 in a state in which a portion of the movable member 120 is inserted into the fixing member 110.

Meanwhile, referring to FIG. 7, due to relative rotation of the fixing member 110 and the movable member 120, the location of the movable member 120 is changed and the length of the movable member 120 is thus changed. As the length of the movable member 120 is changed in this way, the entire length of the body 100 is changed.

Accordingly, the location of the indenter 200 located at the lower end of the body 100 is changed in conjunction.

In this way, in the body 100 according to the present invention, as the fixing member 110 is coupled to the objective lens 10 and the indenter 200 is coupled to the lower end of the movable member 120, the spaced distance between the objective lens 10 and the indenter 200 is adjusted in accordance with a change in the length of the movable member 120.

In detail, as illustrated, in a state in which the movable member 120 is moved downward from the fixing member 110, the spaced distance between the indenter 200 and the objective lens 10 is L2.

Further, in a state in which the spaced distance between the objective lens 10 and the indenter 200 is L2, mutual rotation of the fixing member 110 and the movable member 120 is restrained, so that the spaced distance between the indenter 200 and the objective lens 10 may be maintained to be L2.

In this way, the spaced distance between the objective lens 10 and the indenter 200 is adjusted and maintained, so that the user may measure the cell tissue C by selectively adjusting the focus of the objective lens 10.

As described above, although the specific embodiments of the present invention have been described and illustrated, the present invention is not limited to the above-described embodiments, and it is obvious to those skilled in the art that the present invention may be variously modified and changed without departing from the spirit and the scope of the present invention. Thus, the modifications and the changes should not be individually understood from the technical spirit and the perspective of the present invention, and modified embodiments belong to the appended claims of the present invention.

The invention claimed is:

1. A lens-attached tissue cell pressurization device that is selectively coupled to an objective lens to perform pressurization in an optical device configured to measure a cell tissue using the objective lens, the lens-attached tissue cell pressurization device comprising:
   a body extending in a lengthwise direction of the objective lens such that at least a portion of the objective lens is inserted into the body and having a connector selectively fixed to the objective lens; and
   an indenter provided at a lower end of the body, having a penetration part formed at a center of the indenter, and configured to pressurize the cell tissue by a change in a relative location of the objective lens and the cell tissue,
   wherein the indenter is spaced apart from a lower end of the objective lens by a predetermined distance, and a spaced distance between the indenter and the objective lens is maintained,
   wherein the body is configured such that the spaced distance between the indenter and the objective lens is selectively adjusted, and
   wherein the body further comprises:
      a fixing member having the connector and selectively fixed to the objective lens; and
      a movable member which is rotated with respect to the fixing member and of which a location is selectively adjusted depending on the rotation to adjust the spaced distance between the indenter and a lower end of the objective lens.

2. The lens-attached tissue cell pressurization device of claim 1, further comprising a pressure measuring means arranged on the indenter to measure a degree of pressure applied to the cell tissue by the indenter.

3. The lens-attached tissue cell pressurization device of claim 2, wherein the pressure measuring means has an upper cell having first coupling parts protruding in a transverse direction from a lower portion of the body and coupled to the body and a lower cell having second coupling parts protruding in a transverse direction from a lower portion of the upper cell and coupled to the indenter.

4. The lens-attached tissue cell pressurization device of claim 3, wherein the first coupling parts and the second coupling parts are arranged to cross each other, and are coupled to the upper cell and the lower cell, respectively.

5. The lens-attached tissue cell pressurization device of claim 1, wherein the penetration part is formed of an optically transparent material, is in contact with the cell tissue and is formed to correspond to a location of the objective lens such that the cell tissue is projected onto the penetration part and is observed through the objective lens.

6. The lens-attached tissue cell pressurization device of claim 1, wherein the spaced distance between the indenter and the objective lens is a focal length of the objective lens.

* * * * *